(12) United States Patent
Shemmeri et al.

(10) Patent No.: US 11,382,805 B1
(45) Date of Patent: Jul. 12, 2022

(54) MEDICATED PATCH APPLICATOR AND ASSOCIATED USE THEREOF

(71) Applicants: Nida Shemmeri, Horseheads, NY (US); Saad Alsamarai, Framingham, MA (US)

(72) Inventors: Nida Shemmeri, Horseheads, NY (US); Saad Alsamarai, Framingham, MA (US)

( * ) Notice: Subject to any disclaimer, the term of this patent is extended or adjusted under 35 U.S.C. 154(b) by 387 days.

(21) Appl. No.: 16/733,848

(22) Filed: Jan. 3, 2020

Related U.S. Application Data

(63) Continuation-in-part of application No. 15/649,589, filed on Jul. 13, 2017, now Pat. No. 10,569,070.

(60) Provisional application No. 62/362,021, filed on Jul. 13, 2016.

(51) Int. Cl.
*A61F 15/00* (2006.01)

(52) U.S. Cl.
CPC .................. *A61F 15/005* (2013.01)

(58) Field of Classification Search
CPC ............ Y10T 156/18; Y10T 156/1705; A61F 15/005; A61B 17/10; A61B 17/085; A45D 2200/1018; B25G 1/02; A47L 13/10; A47L 13/46; A47K 7/028; B26B 19/145; B26B 19/14; B26B 21/523; B26B 19/3853; B26B 19/063; B26B 19/3846; B26B 19/386; A61M 2025/0266; A61M 35/30; A61M 35/006; A61M 35/00
See application file for complete search history.

(56) References Cited

U.S. PATENT DOCUMENTS

| | | | | |
|---|---|---|---|---|
| 4,615,066 | A | * | 10/1986 | Colognori ............... A47L 13/46 401/6 |
| 2005/0274453 | A1 | * | 12/2005 | Anvar ................... A61F 15/005 156/247 |

* cited by examiner

*Primary Examiner* — Ophelia A Hawthorne
(74) *Attorney, Agent, or Firm* — Ashkan Najafi (57) ABSTRACT

A medicated patch applicator includes a handle having a centrally registered longitudinal axis, a frame statically connected to the handle and configured to maintain a fixed spatial relationship therewith, and a generally L-shaped implement coupled to the frame and disposed subjacent to the handle. Such an implement is located adjacent to a juncture of the frame and the handle. The implement arcuately protrudes forwardly from posterior of the handle, traverses the centrally registered longitudinal axis, and terminates anterior of the handle. The implement is capable of removing an existing back liner of an existing medicated patch during an application process of placing the existing medicated patch onto a skin of a user.

19 Claims, 5 Drawing Sheets

MEDICATED PATCH APPLICATOR AND ASSOCIATED USE THEREOF

CROSS REFERENCE TO RELATED APPLICATIONS

This is a continuation-in-part application of U.S. patent application Ser. No. 15/649,589, filed Jul. 13, 2017, now U.S. Pat. No. 10,569,070, which claims the benefit of U.S. provisional patent application No. 62/362,021 filed Jul. 13, 2016, which are both incorporated by reference herein in their entireties.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

Technical Field

Exemplary embodiment(s) of the present disclosure relate to medicated patch applicators and, more particularly, to a manually operated, handheld device which enables an individual to easily apply an adhesive-backed, medicated patch to any area of his or her back. Ideal for consumers suffering back pain and living alone, the medicated patch applicator would permit its users to gain relief from pain, and do so without any assistance to apply the medicated patch.

Prior Art

At one time or another, approximately 80 percent of the populace—four out of every five consumers—will suffer a back injury, or a bout of back pain. And for many who suffer back pain, an over-the-counter, adhesive-backed patch—IcyHot® and Salonpas® being two of the most familiar brands—will bring relief: If, that is, they can get the patch onto the area of their back where it's needed. For those with a spouse, child, or parent in the household, the essential assistance may be close at hand—but for those living alone with back pain, applying the adhesive patch is practically impossible, meaning that the relief it would bring, for all intents and purposes, stays in the box. The invention to be presented and explored in the course of this report would correct this unfortunate situation, and permit the back-pain sufferer to apply the medicated patch to his or her own back.

Most back patches, however effective at alleviating pain or reducing swelling, are practically impossible to apply to one's own back; and to be able to do so, without exacerbating the back pain that made the patch necessary in the first place, would be a major improvement in the lives of people who experience back pain.

Accordingly, a need remains for a medicated patch applicator in order to overcome at least one aforementioned shortcoming. The exemplary embodiment(s) satisfy such a need by providing a manually operated, handheld device that is convenient and easy to use, lightweight yet durable in design, versatile in its applications, and designed for an individual to easily apply an adhesive-backed, medicated patch to any area of his or her back. Ideal for consumers suffering back pain and living alone, the medicated patch applicator would permit its users to gain relief from pain, and do so without any assistance to apply the medicated patch.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a medicated patch applicator for easily applying an adhesive-backed, medicated patch to any area of a user back. These and other objects, features, and advantages of the non-limiting exemplary embodiment(s) are provided by a medicated patch applicator includes a handle having a centrally registered longitudinal axis, a frame statically connected to the handle and configured to maintain a fixed spatial relationship therewith, and a generally L-shaped implement coupled to the frame and disposed subjacent to the handle. Advantageously, such an implement is located adjacent to a juncture of the frame and the handle. Advantageously, the implement arcuately protrudes forwardly from posterior of the handle, traverses the centrally registered longitudinal axis, and terminates anterior of the handle. Advantageously, the implement is capable of removing an existing back liner of an existing medicated patch during an application process of placing the existing medicated patch onto a skin of a user. Such a structural configuration provides the new, useful, and unexpected result of enabling an individual to easily apply an adhesive-backed, medicated patch to any area of his or her back.

In a non-limiting exemplary embodiment, the frame includes a posterior section and an anterior section connected thereto, wherein the posterior section is oriented perpendicular to the anterior section. The frame further includes a plurality of support arms attached to opposed lateral sides of the anterior section, respectively, and a plurality of springs operably attached to the support arms, respectively. A door is operably coupled to the springs and positioned along the anterior section. Advantageously, the door is pivoted between a closed equilibrium position rested on the anterior section and an open tensioned position spaced above the anterior section. Such a structural configuration provides the new, useful, and unexpected result of enabling a user to easily remove the medicated patch back liner during use.

In a non-limiting exemplary embodiment, the frame further includes a roller having axially offset opposed ends rotatably engaged with a distal end of the anterior section.

In a non-limiting exemplary embodiment, the door has a first portion directly attached to the springs and a second portion rested on the anterior section. Such a door further has a handle statically affixed to a distal edge of the second portion adjacent to the roller.

In a non-limiting exemplary embodiment, the posterior section has a substantially Y-shaped configuration.

In a non-limiting exemplary embodiment, the anterior section has a substantially planar top surface.

In a non-limiting exemplary embodiment, the handle includes a first tubular section directly coupled to the frame, a second tubular section telescopically engaged with the first tubular section, an elbow section statically mated to the second tubular section, and a detent operably engaged with the first tubular section and the second tubular section.

In a non-limiting exemplary embodiment, the implement includes a flexible tether anchored to the posterior section of the frame and angled forwardly above the anterior section, and a fastener mated to a distal end of the tether. Advantageously, the tether is disposed above the door when the door is at the closed equilibrium position. Such a structural configuration provides the new, useful, and unexpected result of enabling a user to easily remove the medicated patch back liner during use.

In a non-limiting exemplary embodiment, the fastener is a clip.

The present disclosure further includes a method of utilizing a medicated patch applicator for easily applying an adhesive-backed, medicated patch to any area of a user back. Such a method includes the steps of: providing a handle has a centrally registered longitudinal axis; providing and statically connecting a frame to the handle; the frame maintaining a fixed spatial relationship with the handle; providing and coupling a generally L-shaped implement to the frame; disposing the implement subjacent to the handle; and locating the implement adjacent to a juncture of the frame and the handle. Advantageously, the implement arcuately protrudes forwardly from posterior of the handle, traverses the centrally registered longitudinal axis, and terminates anterior of the handle. Advantageously, the implement is capable of removing an existing back liner of an existing medicated patch during an application process of placing the existing medicated patch onto a skin of a user.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to back liner any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

If used herein, "about" means approximately or nearly and in the context of a numerical value or range set forth means±15% of the numerical.

If used herein, "substantially" means largely if not wholly that which is specified but so close that the difference is insignificant.

Figure 1:
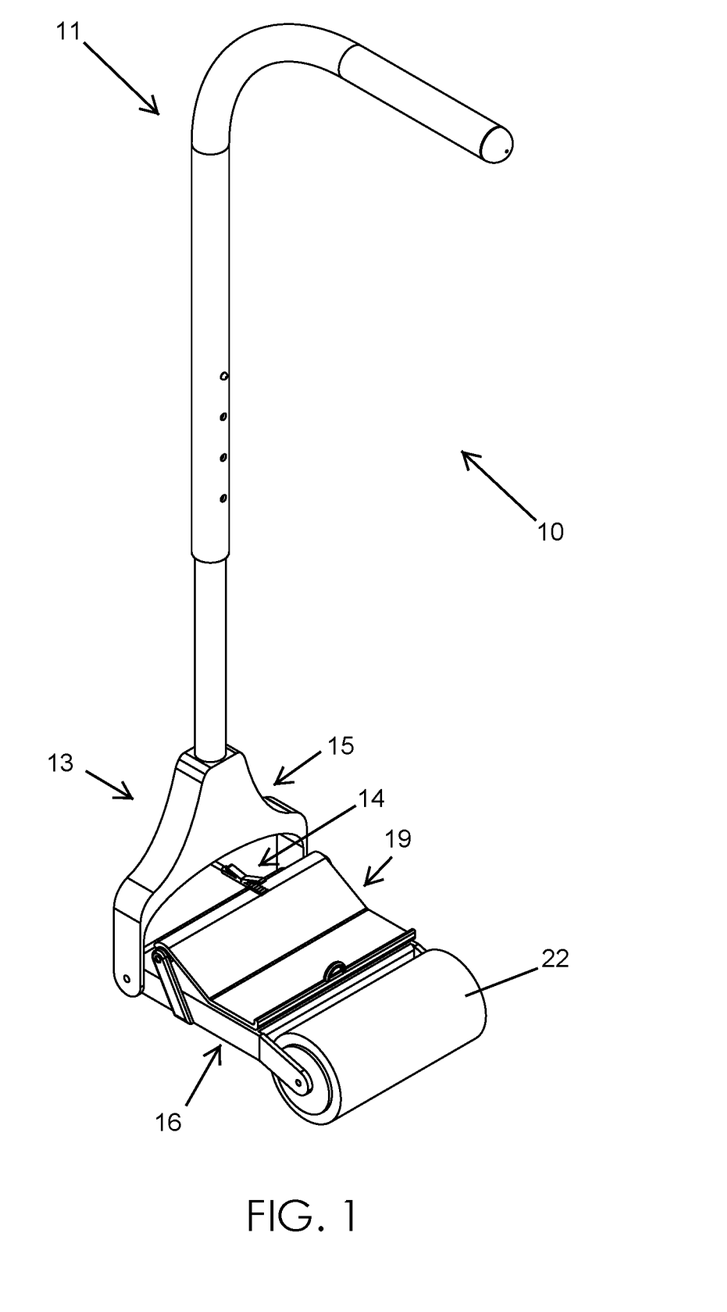
FIG. 1 is a perspective view illustrating a medicated patch applicator, in accordance with a non-limiting exemplary embodiment.
Figure 2:
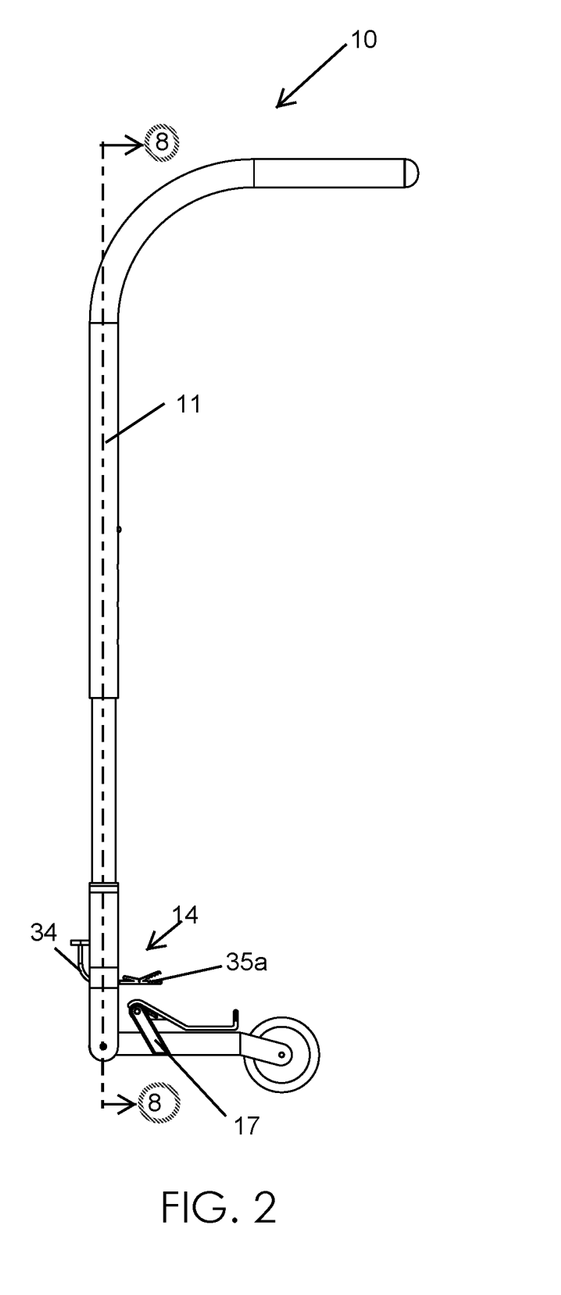
FIG. 2 is a side elevational view of the medicated patch applicator.
Figure 3:
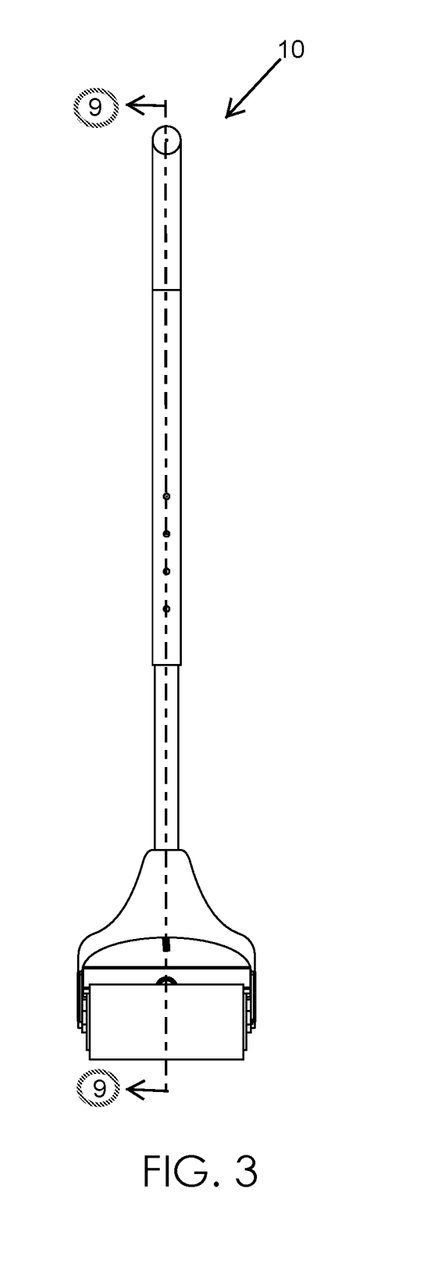
FIG. 3 is a front elevational view of the medicated patch applicator.
Figure 4:
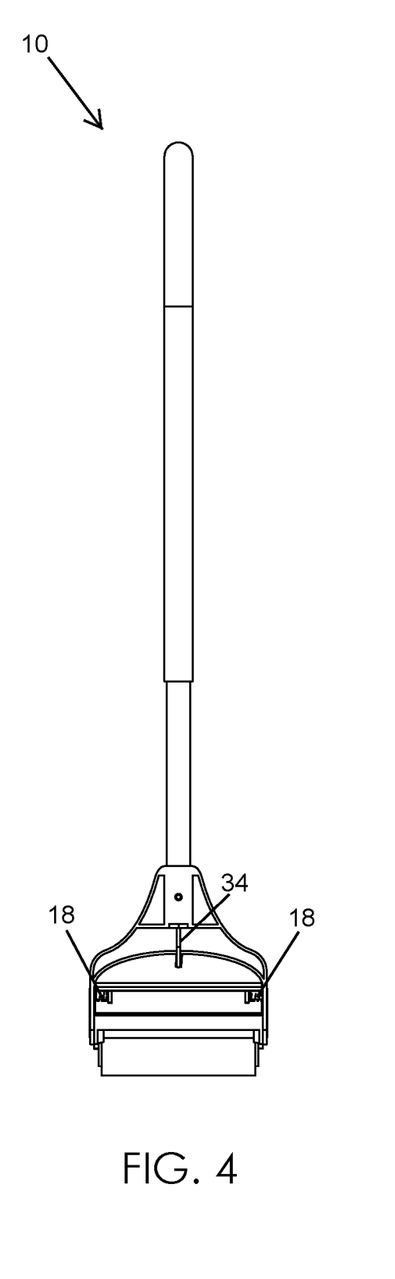
FIG. 4 is a rear elevational view of the medicated patch applicator.
Figure 5:
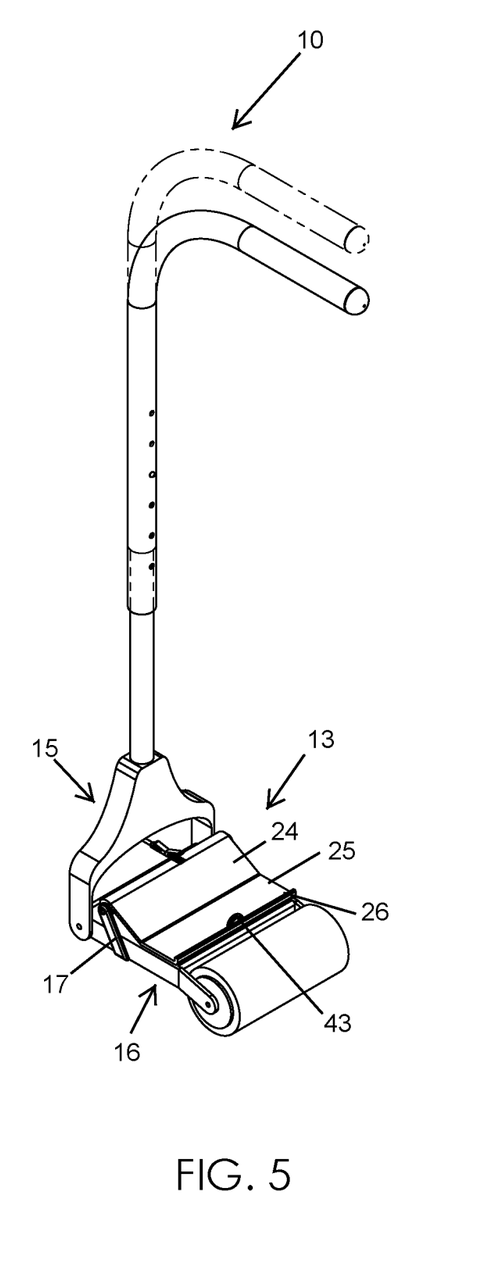
FIG. 5 is perspective view showing a telescopic handle displacement of the medicated patch applicator.
Figure 6:
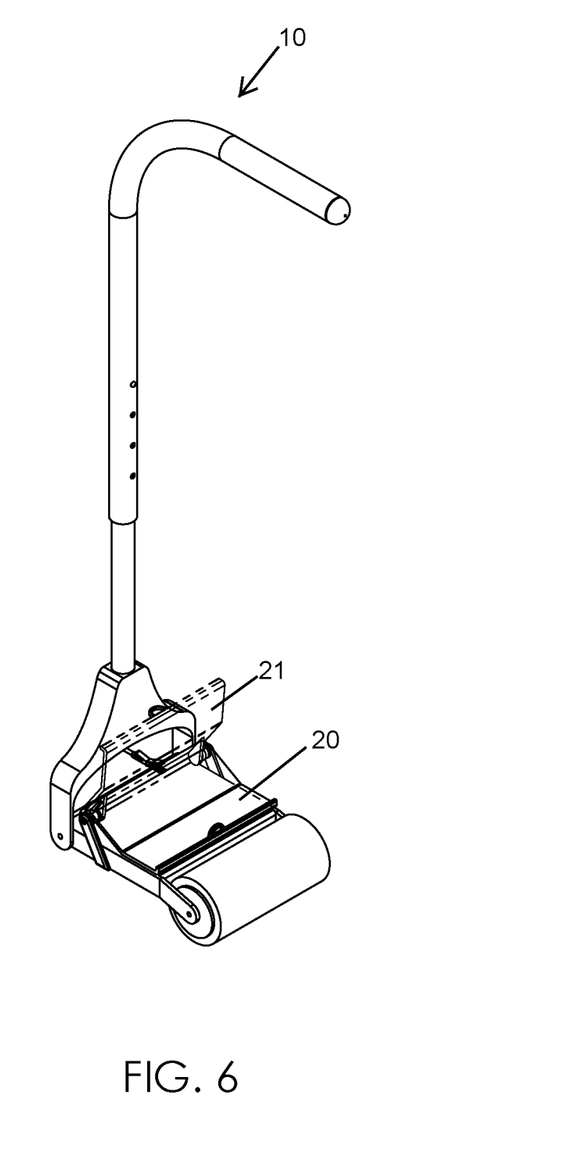
FIG. 6 is a perspective view showing an upward door articulation of the medicated patch applicator.
Figure 7:
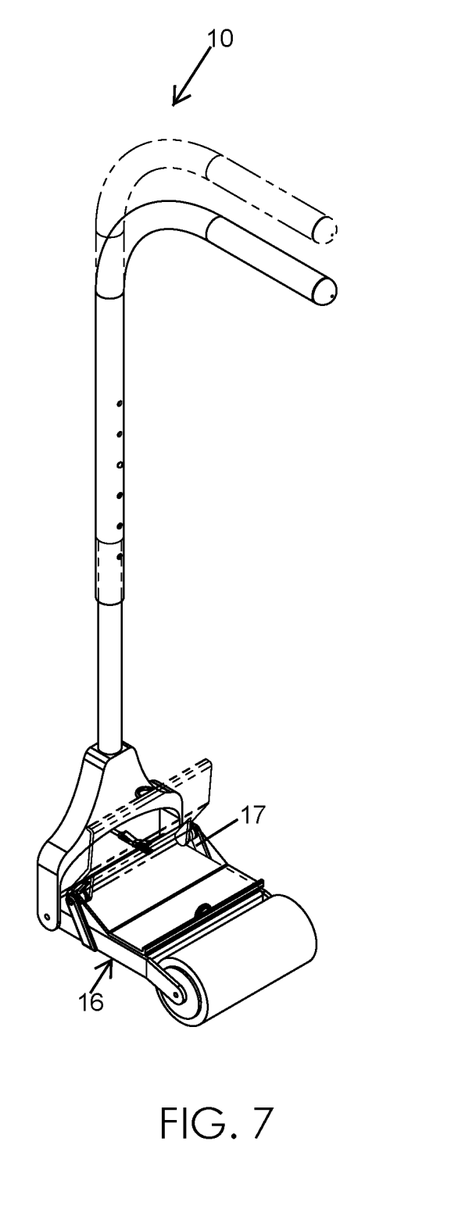
FIG. 7 is a perspective view showing both the upward door articulation and the telescopic handle displacement of the medicated patch applicator.
Figure 8:
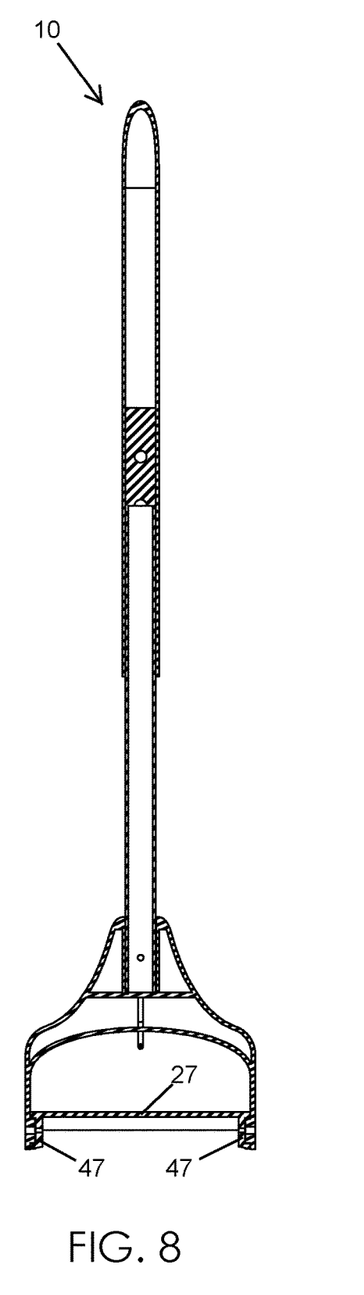
FIG. 8 is a cross-sectional view taken along line 8-8 in FIG. 2.
Figure 9:
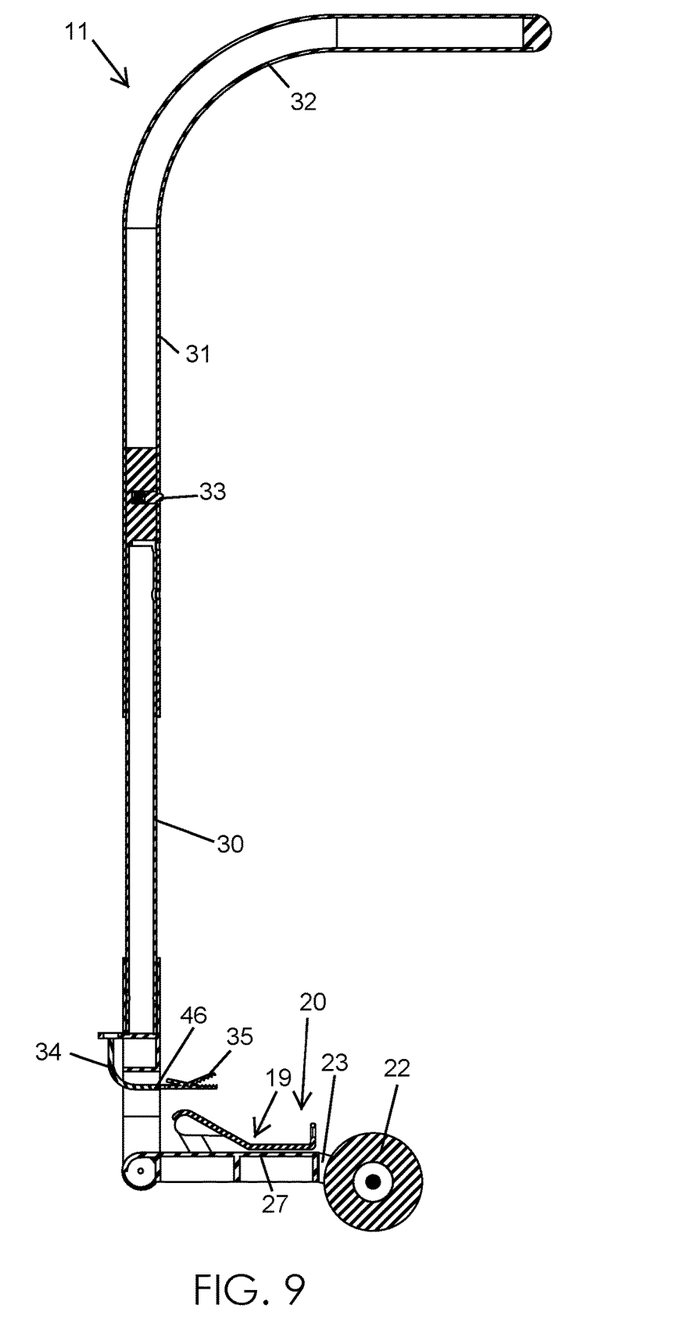
FIG. 9 is a cross-sectional view taken along line 9-9 in FIG. 3.

The non-limiting exemplary embodiment(s) is/are referred to generally in FIGS. 1-9 and is/are intended to provide a medicated patch applicator 10 for easily applying an adhesive-backed, medicated patch to any area of a user back. The medicated patch applicator 10 includes a handle 11 having a centrally registered longitudinal axis 12, a frame 13 statically connected to the handle 11 and configured to maintain a fixed spatial relationship therewith, and a generally L-shaped implement 14 coupled to the frame 13 and disposed subjacent to the handle 11. Advantageously, such an implement 14 is located adjacent to a juncture of the frame 13 and the handle 11. Advantageously, the implement 14 arcuately protrudes forwardly from posterior of the handle 11, traverses the centrally registered longitudinal axis 12, and terminates anterior of the handle 11. Advantageously, the implement 14 is capable of removing an existing back liner of an existing medicated patch during an application process of placing the existing medicated patch onto a skin of a user. Such a structural configuration provides the new, useful, and unexpected result of enabling an individual to easily apply the adhesive-backed, medicated patch to any area of his or her back.

In a non-limiting exemplary embodiment, the frame 13 includes a posterior section 15 and an anterior section 16 connected thereto, wherein the posterior section 15 is oriented perpendicular to the anterior section 16. The frame 13 further includes a plurality of support arms 17 attached to opposed lateral sides of the anterior section 16, respectively, and a plurality of springs 18 operably attached to the support arms, respectively. A door 19 is operably coupled to the springs 18 and positioned along the anterior section 16. Advantageously, the door 19 is pivoted between a closed equilibrium position 20 rested on the anterior section 16 and an open tensioned position 21 spaced above the anterior section 16. Such a structural configuration provides the new, useful, and unexpected result of enabling a user to easily remove the medicated patch back liner before affixing it onto the his/her skin.

In a non-limiting exemplary embodiment, movement of the posterior section 15 is prevented relative to a position of the anterior section 16 by employing built in keys. Thus, there is only one position allowed. Advantageously, such keys 47 help for easy assembling of the parts (as perhaps best shown in FIG. 8).

In a non-limiting exemplary embodiment, the frame 13 further includes a roller 22 having axially offset opposed ends rotatably engaged with a distal end 23 of the anterior section 16.

In a non-limiting exemplary embodiment, the door 19 has a first portion 24 directly attached to the springs 18 and a second portion 25 rested on the anterior section 16. Such a door 19 further has a handle 43 statically affixed to a distal edge 26 of the second portion 25 adjacent to the roller 22.

In a non-limiting exemplary embodiment, the posterior section 15 has a substantially Y-shaped configuration.

In a non-limiting exemplary embodiment, the anterior section 16 has a substantially planar top surface 27.

In a non-limiting exemplary embodiment, the handle 11 includes a first tubular section 30 directly coupled to the frame 13, a second tubular section 31 telescopically engaged with the first tubular section 30, an elbow section 32 statically mated to the second tubular section 31, and a detent 33 operably engaged with the first tubular section 30 and the second tubular section 31.

In a non-limiting exemplary embodiment, the implement 14 includes a flexible tether 34 anchored to the posterior section 15 of the frame 13 and angled forwardly above the anterior section 16, and a fastener 35 mated to a distal end 46 of the tether 34. Advantageously, the tether 34 is disposed above the door 19 when the door 19 is at the closed equilibrium position 20. Such a structural configuration provides the new, useful, and unexpected result of enabling a user to easily remove the medicated patch back liner prior to affixing it to his/her skin. Advantageously, the pulling force of the elastic tether 34 is less than friction force, which holds the medicated patch in place under the pressure of the spring-loaded door 19. Notably, the springs 18 are torsion springs 18 to frictionally push (urge) the door 19 against the medicated patch and provide the required tension on the medicated patch as needed during use.

In a non-limiting exemplary embodiment, the fastener 35 is a clip 35a.

The present disclosure further includes a method of utilizing a medicated patch applicator 10 for easily applying an adhesive-backed, medicated patch to any area of a user back. Such a method includes the steps of: providing a handle 11 has a centrally registered longitudinal axis 12; providing and statically connecting a frame 13 to the handle 11; the frame 13 maintaining a fixed spatial relationship with the handle 11; providing and coupling a generally L-shaped implement 14 to the frame 13; disposing the implement 14 subjacent to the handle 11; and locating the implement 14 adjacent to a juncture of the frame 13 and the handle 11. Advantageously, the implement 14 arcuately protrudes forwardly from posterior of the handle 11, traverses the centrally registered longitudinal axis 12, and terminates anterior of the handle 11. Advantageously, the implement 14 is capable of removing an existing back liner of an existing medicated patch during an application process of placing the existing medicated patch onto a skin of a user.

A non-limiting exemplary embodiment(s) of the present disclosure is referred to generally in FIGS. 1-9 and is intended to provide a manually operated, handheld device which enables an individual to easily apply an adhesive-backed, medicated patch to any area of his or her back. Ideal for consumers suffering back pain and living alone, the medicated patch applicator 10 permits its users to gain relief from pain, and do so without any assistance to apply the medicated patch. It should be understood that the exemplary embodiment(s) may be used to apply a variety of medicated patches, and should not be limited to any particular medicated patch described herein.

Referring to the figures in general, in a non-limiting exemplary embodiment(s), the medicated patch applicator 10 is handheld and manually operated with which an individual user could reach any area of his or her back, and apply an adhesive-backed medicated patch.

In a non-limiting exemplary embodiment, medicated patch applicator 10 may be fabricated in injection-molded thermoplastic, and includes an adjustable, angled handle 11. The handle 11 can measure approximately 16 centimeters (cm) in length and 3 to 5 cm in diameter, and features an angled handle 11 that allows the frame 13 and roller 22 of the medicated patch applicator 10 to extend well down (and across, as the case may be) the user's back, while the handle 11—which is finished with an ergonomic, contoured rubber grip—puts no strain on the user's arm or shoulder joint.

The anterior section 16 is suitably sized and shaped to receive the medicated patch. The medicated patch applicator 10 also features a spring-clip 35a to which the medicated patch liner or backing can be engaged. The medicated patch applicator 10 is rolled down or across the user's back, such that the clip 35a peels away the backing from underneath the patch as the foam roller 22—traveling behind the clip 35a adjacent to the top surface 27 of the patch—applies the patch smoothly and evenly.

The medicated patch applicator 10 provides a "helping hand" when it comes to relieving an aching, strained back—a helping hand that could easily reach the affected area (without further strain), and smoothly apply a medicated, peel-and-stick patch. While conceived and designed primarily for use by persons living on their own, the medicated patch applicator 10 could be used to advantage by virtually any consumer seeking to alleviate back pain with a patch—business travelers away from home; athletes on road-trips; campers and backpackers; boaters, anglers, and hunters, to name but a few.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to back liner all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to back liner all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A medicated patch applicator for easily applying an adhesive-backed, medicated patch to any area of a user back, said medicated patch applicator comprising:
    a handle having a centrally registered longitudinal axis;
    a frame statically connected to said handle and configured to maintain a fixed spatial relationship therewith; and
    an implement coupled to said frame and disposed subjacent to said handle, said implement being located adjacent to a juncture of said frame and said handle wherein said implement arcuately protrudes forwardly from posterior of said handle, traverses the centrally registered longitudinal axis, and terminates anterior of said handle;
    wherein said implement is capable of removing an existing back liner of an existing medicated patch during an application process of placing the existing medicated patch onto a skin of a user.

2. The medicated patch applicator of claim 1, wherein said frame comprises:
    a posterior section and an anterior section connected thereto, said posterior section being oriented perpendicular to said anterior section;
    a plurality of support arms attached to opposed lateral sides of said anterior section, respectively;
    a plurality of springs operably attached to said support arms, respectively; and
    a door operably coupled to said springs and positioned along said anterior section, wherein said door is pivoted between a closed equilibrium position rested on said anterior section and an open tensioned position spaced above said anterior section.

3. The medicated patch applicator of claim 2, wherein said frame further comprises: a roller having axially offset opposed ends rotatably engaged with a distal end of said anterior section.

4. The medicated patch applicator of claim 3, wherein said door has a first portion directly attached to said springs and a second portion rested on said anterior section, said door further having a handle statically affixed to a distal edge of said second portion adjacent to said roller.

5. The medicated patch applicator of claim 2, wherein said implement comprises:
    a flexible tether anchored to said posterior section of said frame and angled forwardly above said anterior section; and
    a fastener mated to a distal end of said tether, said tether being disposed above said door when said door is at said closed equilibrium position.

6. The medicated patch applicator of claim 1, wherein said handle comprises:
    a first tubular section directly coupled to said frame;
    a second tubular section telescopically engaged with said first tubular section;
    an elbow section statically mated to said second tubular section; and
    a detent operably engaged with said first tubular section and said second tubular section.

7. The medicated patch applicator of claim 6, wherein said fastener is a clip.

8. The medicated patch applicator of claim 1, wherein said posterior section has a substantially Y-shaped configuration.

9. The medicated patch applicator of claim 1, wherein said anterior section has a substantially planar top surface.

10. A medicated patch applicator for easily applying an adhesive-backed, medicated patch to any area of a user back, said medicated patch applicator comprising:
    a handle having a centrally registered longitudinal axis;
    a frame statically connected to said handle and configured to maintain a fixed spatial relationship therewith; and
    an implement coupled to said frame and disposed subjacent to said handle, said implement being located adjacent to a juncture of said frame and said handle wherein said implement arcuately protrudes forwardly from posterior of said handle, traverses the centrally registered longitudinal axis, and terminates anterior of said handle;

wherein said implement is capable of removing an existing back liner of an existing medicated patch during an application process of placing the existing medicated patch onto a skin of a user;

wherein said implement is generally L-shaped.

11. The medicated patch applicator of claim 10, wherein said frame comprises:
a posterior section and an anterior section connected thereto, said posterior section being oriented perpendicular to said anterior section;
a plurality of support arms attached to opposed lateral sides of said anterior section, respectively;
a plurality of springs operably attached to said support arms, respectively; and
a door operably coupled to said springs and positioned along said anterior section, wherein said door is pivoted between a closed equilibrium position rested on said anterior section and an open tensioned position spaced above said anterior section.

12. The medicated patch applicator of claim 11, wherein said frame further comprises: a roller having axially offset opposed ends rotatably engaged with a distal end of said anterior section.

13. The medicated patch applicator of claim 12, wherein said door has a first portion directly attached to said springs and a second portion rested on said anterior section, said door further having a handle statically affixed to a distal edge of said second portion adjacent to said roller.

14. The medicated patch applicator of claim 11, wherein said implement comprises:
a flexible tether anchored to said posterior section of said frame and angled forwardly above said anterior section; and
a fastener mated to a distal end of said tether, said tether being disposed above said door when said door is at said closed equilibrium position.

15. The medicated patch applicator of claim 10, wherein said handle comprises:
a first tubular section directly coupled to said frame;
a second tubular section telescopically engaged with said first tubular section;
an elbow section statically mated to said second tubular section; and
a detent operably engaged with said first tubular section and said second tubular section.

16. The medicated patch applicator of claim 15, wherein said fastener is a clip.

17. The medicated patch applicator of claim 10, wherein said posterior section has a substantially Y-shaped configuration.

18. The medicated patch applicator of claim 10, wherein said anterior section has a substantially planar top surface.

19. A method of utilizing a medicated patch applicator for easily applying an adhesive-backed, medicated patch to any area of a user back, said method comprising the steps of:
providing a handle having a centrally registered longitudinal axis;
providing and statically connecting a frame to said handle;
said frame maintaining a fixed spatial relationship with said handle;
providing and coupling an implement to said frame;
disposing said implement subjacent to said handle; and
locating said implement adjacent to a juncture of said frame and said handle wherein said implement arcuately protrudes forwardly from posterior of said handle, traverses the centrally registered longitudinal axis, and terminates anterior of said handle;
wherein said implement is capable of removing an existing back liner of an existing medicated patch during an application process of placing the existing medicated patch onto a skin of a user;
wherein said implement is generally L-shaped.

* * * * *